(12) United States Patent
Landis et al.

(10) Patent No.: US 11,406,780 B2
(45) Date of Patent: Aug. 9, 2022

(54) ENDOTRACHEAL TUBE SECUREMENT DEVICES AND METHODS

(71) Applicant: WESTMED INC., Tucson, AZ (US)

(72) Inventors: Robert M. Landis, Mountainside, NJ (US); Robert Tero, Bayonne, NJ (US)

(73) Assignee: WESTMED INC., Tucson, AZ (US)

( * ) Notice: Subject to any disclaimer, the term of this patent is extended or adjusted under 35 U.S.C. 154(b) by 469 days.

(21) Appl. No.: 16/421,561

(22) Filed: May 24, 2019

(65) Prior Publication Data
US 2019/0358421 A1 Nov. 28, 2019

Related U.S. Application Data

(60) Provisional application No. 62/676,545, filed on May 25, 2018.

(51) Int. Cl.
*A61M 16/04* (2006.01)
*A61M 25/02* (2006.01)

(52) U.S. Cl.
CPC ... *A61M 16/0497* (2013.01); *A61M 2025/022* (2013.01); *A61M 2025/0206* (2013.01); *A61M 2025/026* (2013.01); *A61M 2025/028* (2013.01); *A61M 2240/00* (2013.01)

(58) Field of Classification Search
CPC .... A61M 2025/022; A61M 2025/0253; A61M 2025/026; A61M 2025/028; A61M 25/02; A61M 2025/0206; A61M 2240/00; A61M 16/0497; A61M 16/0488; A61M 2025/0213; A61M 2025/0226; A61M 2025/0246
See application file for complete search history.

(56) References Cited

U.S. PATENT DOCUMENTS

| | | | |
|---|---|---|---|
| 3,422,817 A | 1/1969 | Mishkin et al. | |
| 3,585,997 A | 6/1971 | Ancerewicz, Jr. | |
| 3,834,380 A | 9/1974 | Boyd | |
| 3,878,849 A | 4/1975 | Muller et al. | |
| 3,924,636 A * | 12/1975 | Addison | A61M 25/02 128/206.25 |
| 3,946,742 A * | 3/1976 | Eross | A61M 16/0488 128/207.17 |
| 4,088,136 A | 5/1978 | Hasslinger et al. | |
| 4,378,012 A * | 3/1983 | Brown | A61M 16/0488 128/207.17 |
| 4,397,647 A * | 8/1983 | Gordon | A61M 25/02 128/DIG. 26 |
| 4,445,894 A | 5/1984 | Kovacs | |
| 4,569,348 A | 2/1986 | Hasslinger | |
| 4,571,245 A | 2/1986 | Hubbard et al. | |

(Continued)

FOREIGN PATENT DOCUMENTS

| | | | | |
|---|---|---|---|---|
| EP | 0145142 A1 | 6/1985 | | |
| EP | 0916361 A1 * | 5/1999 | | A61M 25/02 |

*Primary Examiner* — Nilay J Shah
(74) *Attorney, Agent, or Firm* — Carter, DeLuca & Farrell LLP

(57) ABSTRACT

ET securement devices and methods are provided wherein the ET securement devices generally include two portions: a first portion for securing an ET tube and a second portion for attaching to the patient. The first portion is configured to releasably attach to the second portion to secure the ET tube relative to the patient.

16 Claims, 8 Drawing Sheets

(56) References Cited

U.S. PATENT DOCUMENTS

| | | | |
|---|---|---|---|
| 4,742,824 A * | 5/1988 | Payton | A61M 16/0666 |
| | | | 128/207.18 |
| 5,000,741 A | 3/1991 | Kalt | |
| 5,038,778 A | 8/1991 | Lott | |
| 5,058,579 A | 10/1991 | Terry et al. | |
| 5,292,312 A | 3/1994 | Delk et al. | |
| 5,345,931 A * | 9/1994 | Battaglia, Jr. | A61M 16/0488 |
| | | | 128/207.17 |
| 5,411,484 A | 5/1995 | Shattuck | |
| 5,490,504 A * | 2/1996 | Vrona | A61M 16/0488 |
| | | | 128/207.14 |
| 5,551,421 A * | 9/1996 | Noureldin | A61M 16/0488 |
| | | | 128/207.17 |
| 5,626,565 A | 5/1997 | Landis et al. | |
| 5,692,268 A | 12/1997 | Case | |
| 5,800,402 A * | 9/1998 | Bierman | A61M 25/02 |
| | | | 128/DIG. 26 |
| 5,879,335 A | 3/1999 | Martinez et al. | |
| 5,918,599 A | 7/1999 | Shesol | |
| 6,050,263 A | 4/2000 | Choksi et al. | |
| 2007/0235034 A1 | 10/2007 | Weaver | |
| 2009/0126740 A1 | 5/2009 | Loescher | |
| 2009/0211573 A1 * | 8/2009 | Russo | A61M 16/0488 |
| | | | 128/200.26 |
| 2014/0261463 A1 * | 9/2014 | Visconti | A61M 16/0497 |
| | | | 128/861 |
| 2016/0121067 A1 * | 5/2016 | VanMiddendorp | |
| | | | A61M 16/0875 |
| | | | 128/207.17 |

* cited by examiner

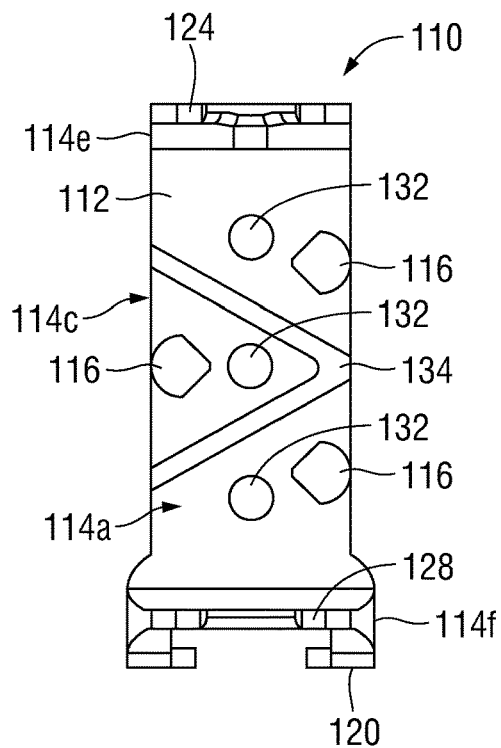
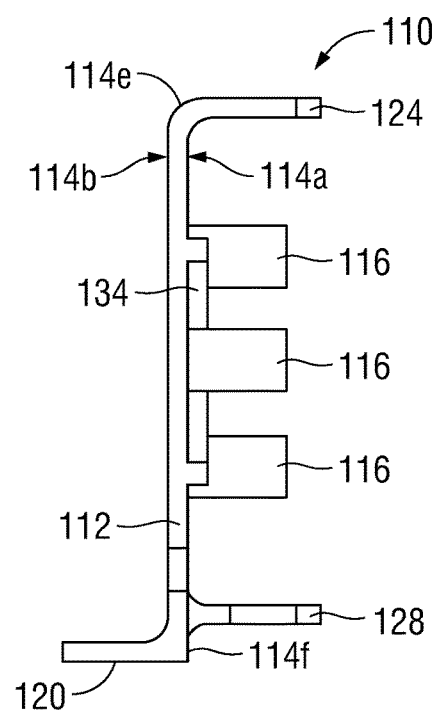
FIG. 1
FIG. 2
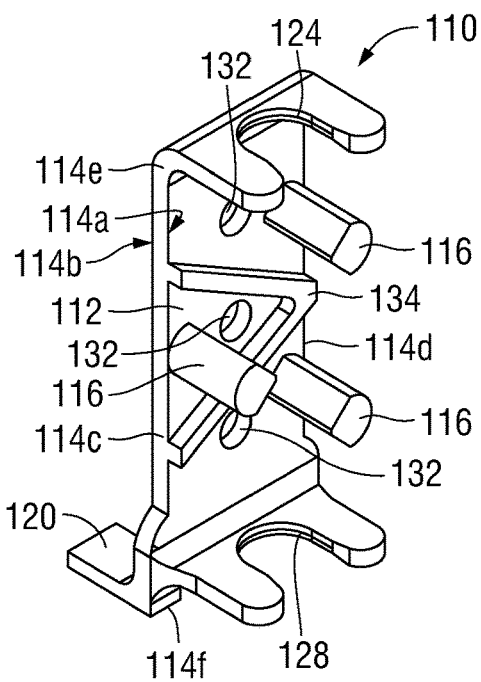
FIG. 3

ENDOTRACHEAL TUBE SECUREMENT DEVICES AND METHODS

CROSS-REFERENCE TO RELATED APPLICATIONS

This application claims the benefit of and priority to U.S. Provisional Patent Application No. 62/676,545, filed on May 25, 2018, the entire contents of which are hereby incorporated herein by reference.

BACKGROUND

Technical Field

The present disclosure relates to medical devices, and more particularly, to devices and methods for securing endotracheal (ET) tubes to a patient, e.g., an infant.

Background of Related Art

There are several devices and methods for securing ET tubes to patients receiving respiratory assistance. One common method utilizes adhesive tape to secure the ET tube in position. However, adhesive tape suitable for skin contact may not be suitable for adhering to the ET Tube, and vice versa. Thus, the practice of wrapping adhesive tape around the ET tube and onto the patient's face is another common practice. While this is a common practice, it is also a tedious and laborious chore.

Devices used to grip the ET tube without the use of adhesives attaching the tube to the skin are described, for example, in U.S. Pat. No. 5,626,565 to Landis ("Landis") and U.S. Pat. No. 6,050,263, to Choksi ("Choski"). Landis discloses a device having a vertical structure and a hook and loop wrap that goes around the ET tube to hold the ET tube against the structure. A strap having clips with points is urged against the outer surface of the ET tube as the strap is wrapped around. The points grip and hold the ET tube in place. While this device and method are successful, they can still be improved.

Choksi discloses a device that uses a U-shaped rigid bar that attaches to the patient's face adjacent the mouth on each side. The rigid bar has an area where the ET tube intersects. This area allows for wrapping of adhesive tape around the ET tube to secure it to the rigid bar. This device and method utilizes adhesive attachment of the ET tube to the bar and adhesive attachment of the bar to the patient's face. However, while this device and method are also successful, they can still be improved upon.

As such, there is a continuing need for a more efficient, effective, and ergonomic securing device and method.

SUMMARY

With respect to securing ET tubes to infants, e.g., premature, neonatal, and/or newborn infants, there are several design constraints and considerations to be taken into account such as, for example: the size of an infant's trachea; the dimensions of the ET tube (typically a 2.5 mm inner diameter and a 4.0 mm outer diameter); that the wall of the ET tube can easily be deformed or crushed, causing restriction to flow and increased work of breathing for the patient; and that an infant's skin is fragile and easily damaged.

Additionally, there are times when the ET tube has been in place for a day or two and the clinician wants to move it to prevent damage to the patient's palate. There are also times when the ET tube needs to be repositioned because it moved too far down into the lung. Further still, there are times when the clinician wants to change the size of the ET tube.

Given the above constraints, considerations, and use-related needs, it may be beneficial, depending upon the particular situation and/or circumstances, to provide an ET Tube securement device and method having one or more of the following: a quick and secure grip to the ET tube without causing restriction to flow; an intuitive and ergonomic quick and secure grip as clinicians may be confronted with the device without training or instructions; features to inhibit unintentional misuse; easy release for ET tube depth adjustment; repositionable in the patient's mouth without requiring removing and reapplication of adhesive tape to the patent's skin; and secure, non-irritating adhesive applied to the skin that is releasable with minimal trauma.

The present disclosure takes into account the above constraints, considerations, and use-related needs to provide efficient, effective, and ergonomic securing devices and methods for securing an ET tube to a patient, e.g., an infant. The above-noted features are exemplified in one or more of the aspects of the present disclosures. These and other aspects of the present disclosures are detailed hereinbelow.

In aspects of the present disclosure, an ET tube securement device is provided including two portions. The first portion includes a tube gripping vertical structure with a face side that has a channel defined by posts where the ET tube can be snapped into and secured from sliding vertically, e.g., up or down. The back side of the vertical structure includes strap arms that wrap around the face side of the vertical structure to hold the ET tube in place. The strap arms may be part of a hook/loop material disposed on the back side of the vertical structure or may include a hook/loop material (or other suitable releasable engagement mechanism) to enable the strap arms to be secured in position. If the ET tube needs to be positioned up or down, the strap arms are unwrapped, the ET tube is peeled out of the channel, is adjusted up or down as needed, and is then snapped back into the channel and secured with the strap arms.

The second portion includes a hook/loop material (or other suitable releasable engagement mechanism) that is laminated first with a soft foam and then a neonatal skin friendly (silicone or hydrocolloid) adhesive for attaching to a patient's face, although other configurations, including different methods of attaching the foam and/or adhesives, other adhesives, etc., are also contemplated.

A base of the first portion includes a hook/loop material (or other suitable releasable engagement mechanism), which may be the same as or separate from the hook/loop material disposed on the back side of the vertical structure and including the strap arms. The hook/loop material is configured to connect to the hook/loop material of the second portion to secure the first portion to the patient's face via the second portion. The first portion may be placed anywhere on the second portion and can be released and moved to any other area on the second portion. The first portion is secured to the second portion via the interconnecting hook and loop fasteners of the respective hook/loop materials thereof. The base of the first portion may extend in perpendicular orientation relative to the vertical structure thereof such that the base of the first portion can be secure to the second portion in parallel orientation therewith and generally parallel to the patient's face, while the vertical structure extends generally perpendicularly therefrom, in a vertical orientation when considering a lying patient. Once the first portion is attached to the second portion, or prior thereto, the ET tube is snapped into the channel and secured therein with the strap arms.

In aspects of the present disclosure, a securement device for securing an ET tube relative to a patient is provided including a vertical support and an attachment member. The vertical support includes a body, a plurality of posts extending from a first face of the body to define a tortuous path extending from a top end of the body to a bottom end of the body. The vertical support further includes first and second guides disposed at or adjacent to the top and bottom ends, respectively, of the body and defining an entry and an exit, respectively. The vertical support is configured to engage an ET tube at the entry via the first guide, within the tortuous path via the plurality of posts, and at the exit via the second guide. The attachment member is attached to the vertical support and includes at least one arm configured to wrap around the vertical support to retain the ET tube therein.

In an aspect of the present disclosure, the device further includes a piece of material configured for positioned on a patient's face at least partially surrounding the patient's mouth. The attachment member is configured to releasably engage the piece of material to thereby releasably engage the vertical support to the piece of material.

In another aspect of the present disclosure, the attachment member is configured to releasably engage the piece of material via hook and loop engagement.

In another aspect of the present disclosure, the vertical support further includes a foot extending from the second face of the body in perpendicular orientation relative to the body. The attachment member includes a base attached to the foot. The base of the attachment member is configured to releasably engage the piece of material.

In still another aspect of the present disclosure, the piece of material includes an adhesive layer configured to adhere to a patient's face. Alternatively or additionally, a support including at least one strap is configured to wrap at least partially around a patients head and engage the piece of material to retain the piece of material on the patient's face.

In yet another aspect of the present disclosure, the vertical support further includes a V-shaped protrusion extending from the front face of the body. The V-shaped protrusion is configured to maintain a minimum gap between a portion of the ET tube and the front face of the body.

In still yet another aspect of the present disclosure, the V-shaped protrusion extends across the tortuous path at least twice.

Another securement device for securing an ET tube relative to a patient provided in accordance with aspects of the present disclosure includes a first portion and a second portion. The first portion includes a vertical support including a body, a plurality of posts extending from the body to define a tortuous path extending from a top of the bottom to a bottom of the body, and first and second guides disposed at or adjacent the top and bottom ends, respectively, of the body and defining an entry and an exit, respectively. The vertical support is configured to engage an ET tube at the entry via the first guide, within the tortuous path via the plurality of posts, and at the exit via the second guide. The first portion further includes an attachment member attached to the vertical support and including at least one arm configured to wrap around the vertical support to retain the ET tube therein. The second portion includes a piece of material configured for positioned on a patient's face at least partially surrounding the patient's mouth and a support including at least one strap configured to wrap at least partially around the patients head and engage the piece of material to retain the piece of material on the patient's face. The first portion is configured to releasably engage the second portion.

In an aspect of the present disclosure, the attachment member is configured to releasably engage the piece of material via hook and loop engagement.

In another aspect of the present disclosure, one of the at least one arms is configured to wrap around the vertical support and the ET tube and engage the piece of material.

A method of securing an ET tube relative to a patient provided in accordance with the present disclosure includes positioning a piece of material about a patients mouth and an ET tube extending into the patients' mouth, engaging a vertical support to the ET tube such that the ET tube extends through a tortuous path defined by the vertical support, wrapping at least one first arm about at least a portion of the vertical support and the ET tube to secure the ET tube, and releasably engaging the vertical support with the piece of material to thereby retain the ET tube relative to the patient.

In an aspect of the present disclosure, engaging the vertical support with the piece of material includes at least one of releasably engaging a base of an attachment member that is attached to the vertical support to the piece of material, or wrapping at least one second arm about at least a portion of the vertical support and the ET tube and releasably engaging the at least one second strap to the piece of material.

In another aspect of the present disclosure, the method further includes positioning a support including at least one strap at least partially around the patients head, and releasably engaging the at least one strap with the piece of material to retain the piece of material on the patient's face.

In still another aspect of the present disclosure, the method further includes disengaging the vertical support from the piece of material and subsequently reengaging the vertical support with the piece of material in at least one of a different position or a different orientation.

In yet another aspect of the present disclosure, engaging the vertical support to the ET tube further includes engaging the ET tube within first and second guides at top and bottom ends, respectively, of the vertical support.

BRIEF DESCRIPTION OF THE DRAWINGS

FIG. 1 is a front view of a vertical support of an ET tube securement device provided in accordance with the present disclosure;

FIG. 2 is a side view of the vertical support of FIG. 1;

FIG. 3 is an isometric view of the vertical support of FIG. 1;

DETAILED DESCRIPTION

ET securement devices and methods are provided in accordance with the present disclosure. The ET securement devices generally include two portions: a first portion for securing an ET tube and a second portion for attaching to the patient. The first portion is configured to releasably attach to the second portion to secure the ET tube relative to the patient.

Figure 4:
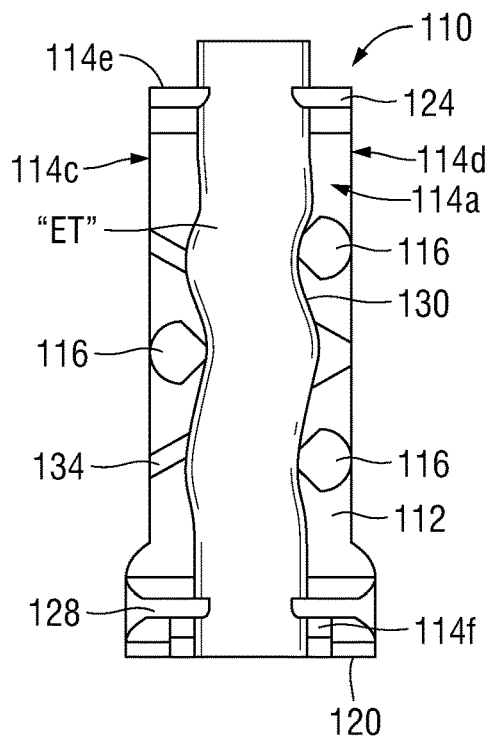
FIG. 4 is a front view of the vertical support of FIG. 1 including an ET tube engaged within the vertical support, illustrating the tortuous path defined by the vertical support for retaining the ET tube therein.
Figure 5:
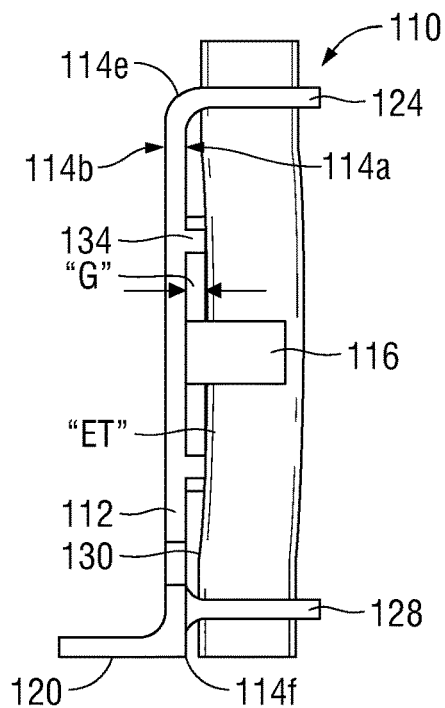
FIG. 5 is a side view of the vertical support of FIG. 1 with the ET tube engaged within the vertical support, illustrating front to back path deformation of the ET tube relative to the vertical support.
Figure 6:
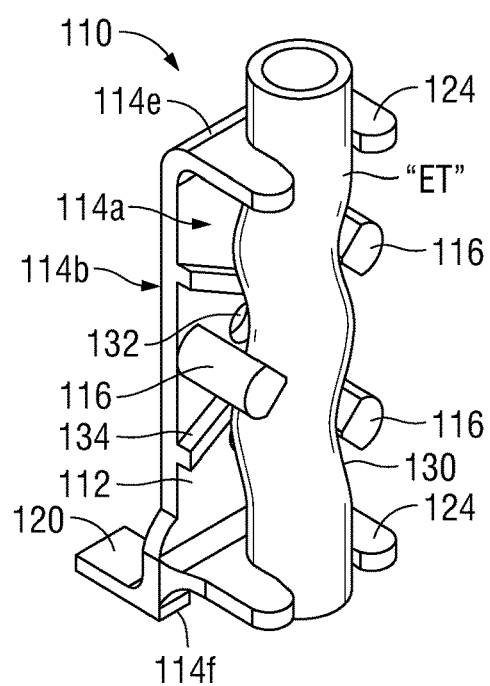
FIG. 6 is an isometric view of the vertical support of FIG. 1 with the tube engaged within the vertical support, illustrating seven (7) points of contact for retention of the ET tube within the vertical support.
Figure 8:
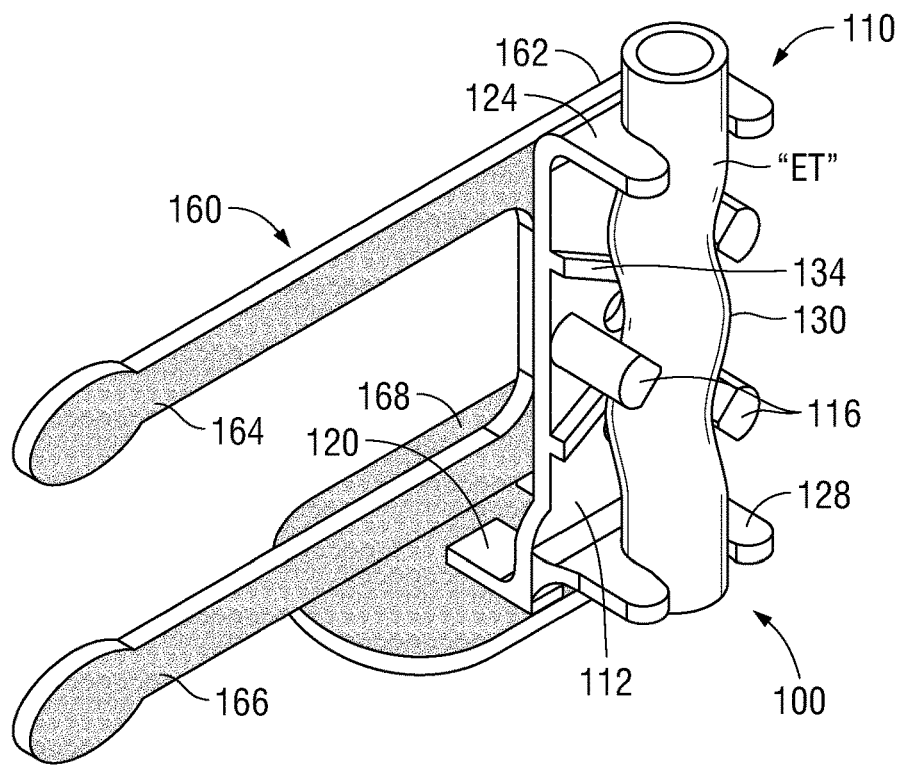
FIG. 8 is an isometric view illustrating the attachment member of FIG. 7 attached to the vertical support of FIG. 1 with the ET tube engaged within the vertical support.
Figure 9:
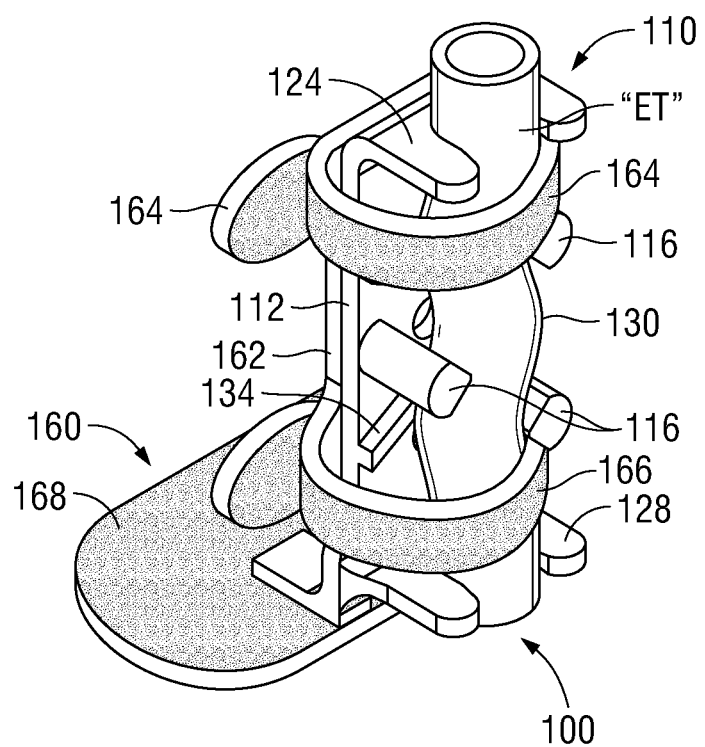
FIG. 9 is an isometric view illustrating the attachment member of FIG. 7 attached to the vertical support of FIG. 1 with the ET tube engaged within the vertical support, wherein straps of the attachment member are wrapped around the ET tube to hold it in place.
Figure 10:
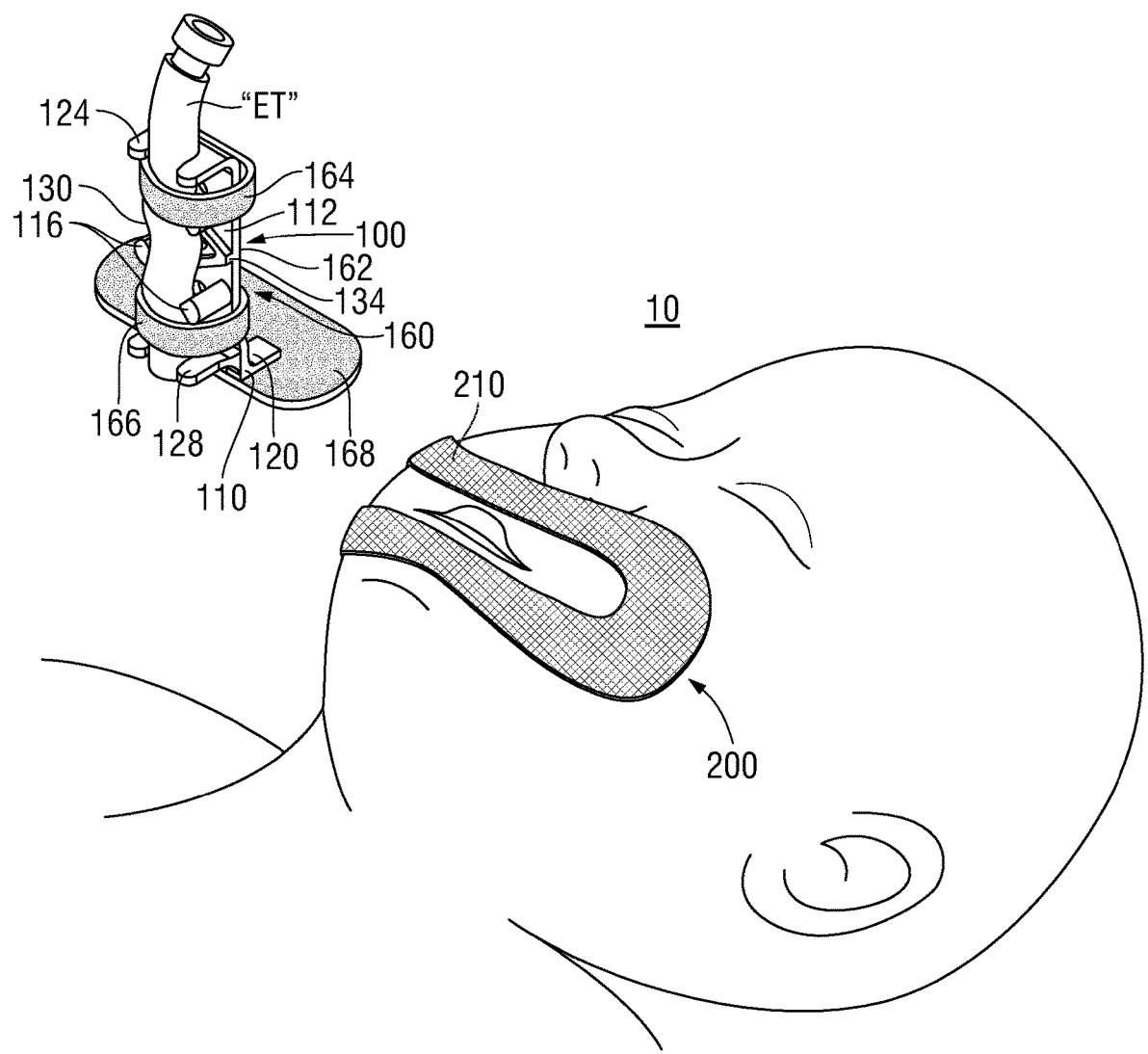
FIG. 10 is a perspective view illustrating a base of the ET tube securement device disposed on an infant's face prior to coupling the remainder of the ET tube securement device thereto.

With general reference to FIGS. 1-10, an ET securement device provided in accordance with the present disclosure is shown generally identified by reference numeral 10 (FIGS. 10 and 11) and includes a first portion 100 (FIGS. 1-9) and a second portion 200 (FIG. 10). First portion 100 generally includes a vertical support 110 (FIGS. 1-3) and an attachment member 160 (FIGS. 4-6).

Referring to FIGS. 1-3, vertical support 110 includes a body 112, a plurality of guide posts 116, a foot 120, and top and bottom guides 124, 128, respectively. Different size verticals supports 110 may be provided as part of a kit, thus enabling an appropriate-sized vertical support 100 to be selected for use depending upon the diameter of the ET tube "ET" used.

Body 112 of vertical support defines a front face 114a, a rear face 114b, opposing sides 114c, 114d, a top end 114e, and a bottom end 114f Guide posts 116 protrude from front face 114a of body 112 in generally perpendicular orientation relative to a plane defined by front face 114a of body 112. Guide posts 116 are arranged to define a tortuous channel 130 for receipt and retention of an ET tube "ET" therein (see FIGS. 4-6). "Tortuous channel" as utilized herein refers to a channel that is neither linear nor follows a constant-radius arc; rather a "tortuous channel" requires multiple change-of-direction turns within the same plane and/or multiple planes. Tortuous channel 130 thus requires ET tube "ET" to make multiple turns in order to be engaged within vertical support 110. With respect to the different size verticals supports 110, the diameter of tortuous channel 130 may be varied to ensure engagement of different diameter ET tubes "ET."

Vertical support 110 further includes holes 132 defined therethrough from front face 114a to rear face 114b. In addition, a V-shaped protrusion 134 protrudes from front face 114a of body 112 in generally perpendicular orientation relative to the plane defined by front face 114a of body 112, and extends between at least some of guide posts 116. V-shaped protrusion 134 is configured to maintain a minimum gap "G" between a central portion of ET tube "ET" and front face 114a of body 112 of vertical support 110 when ET tube "ET" is engaged therein, thus providing a bend in ET tube "ET" in a top-to-bottom direction when engaged with the vertical structure (see FIG. 5). The top and bottom portions of ET tube "ET" need not necessarily contact front face 114a of body 112 but are, in at least one location each, closer to front face 114a of body 112 than the central portion of ET tube "ET," e.g., a gap defined between each of the top and bottom portions of ET tube "ET" and front face 114a is less than gap "G." The concave side of the bend is oriented towards body 112 and, thus, the convex side of the bend is oriented away from body 112. V-shaped protrusion 134 need not define a pointed apex but, rather, may include a curved apex or linear, e.g., flattened, apex, still constituting a "V" shape.

Foot 120 of vertical support 110 extends from rear face 114b of body 112 in generally perpendicular orientation relative to the plane defined by rear face 114b of body 112. Foot 120 is positioned at or adjacent bottom end 114f of body 112. Top and bottom guides 124, 128 extend from front face 114a of body 112 in generally perpendicular orientation relative to the plane defined by front face 114a of body 112 and are disposed at or adjacent the respective top and bottom ends 114e, 114f of body 112. Guides 124, 128 may define U-shaped configurations wherein the open-end of the U-shaped guides 124, 128 are configured to receive ET tube "ET" therethrough and into engagement in abutment or adjacent the saddles of the U-shaped guides 124, 128, although other configurations are also contemplated. Guides 124, 128 define the entry and exit, respectively, to tortuous channel 130. In other words, tortuous channel 130 extends between guides 124, 128.

Figure 11:
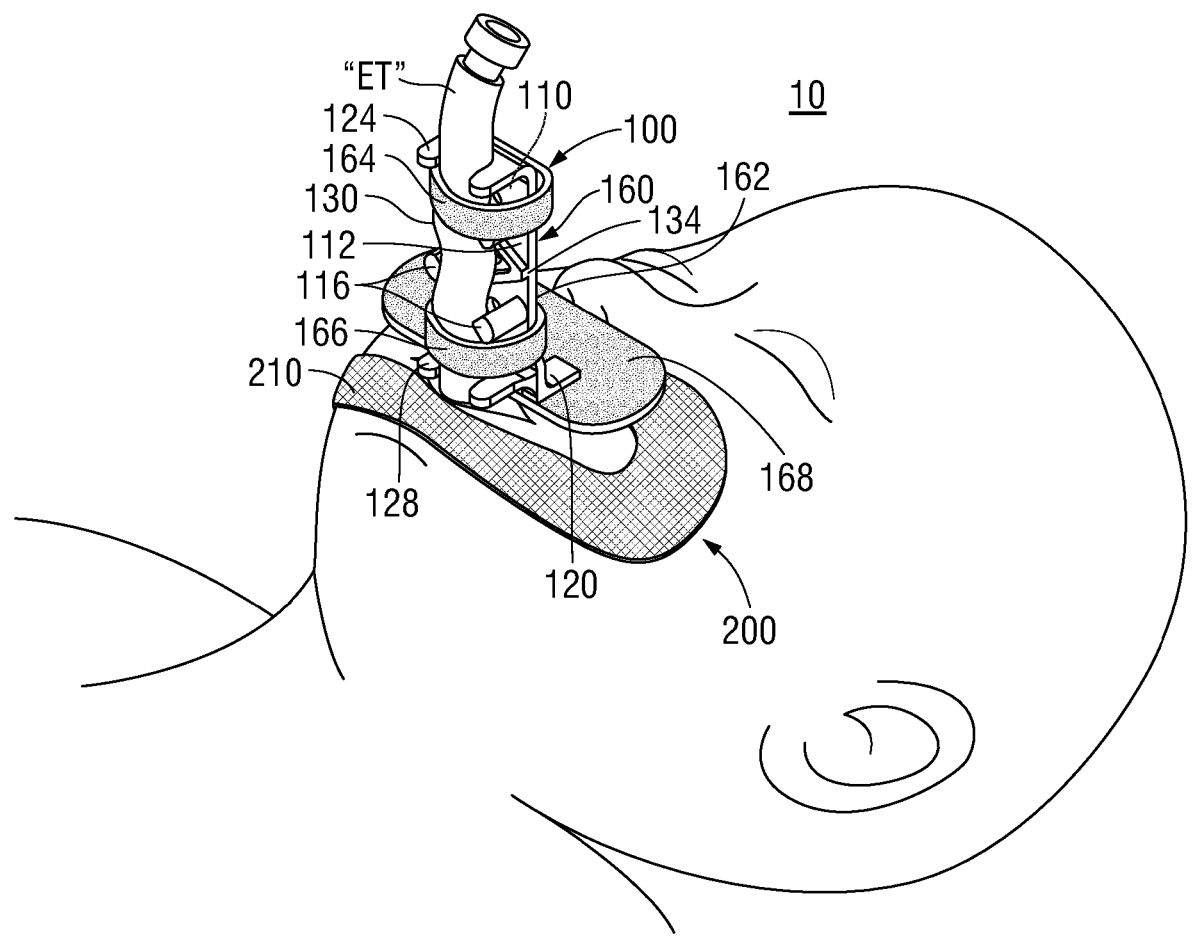
FIG. 11 is a perspective view illustrating the ET tube securement device secured in position on the infant's face retaining an ET tube extending into the infant's mouth.

Referring to FIG. 4-6, ET tube "ET" is shown engaged within vertical support 110 of first portion 100 of ET securement device 10 (FIGS. 10 and 11). More specifically, ET tube "ET" is engaged within and extends from guide 124 at top end 114e of body 112 of vertical support 110, through tortuous channel 130 defined by posts 116, to guide 128 at bottom end 114f of body 112 of vertical support 110. ET tube "ET," as best illustrated in FIG. 4, defines a plurality of bends within a vertical plane parallel to the plane defined by front face 114a of body 112, e.g., bends towards and away from opposing sides 114c, 114d of body 112, and also defines a bend in a vertical plane perpendicular to the plane defined by front face 114a of body 112, e.g., bending towards and away from body 112. The bends in the vertical, parallel plane are due to the positioning of posts 116 to define the tortuous channel 130 while the bend in the vertical, perpendicular plane is due to the V-shaped protrusion 134.

With ET tube "ET" engaged within vertical support 110 as detailed above, posts 116 and guides 124, 128 establish seven (7) points of contact between the ET tube "ET" and vertical support 110 (one by each post 116 and two by each guide 124, 128). These contact points maintain engagement of ET tube "ET" within vertical support 110 while reducing the chance of over-deforming ET tube "ET" in one area, which could result in flow restriction. These contact points also helps prevent misuse via over-tightening or over-gripping, which may likewise cause flow restriction.

Figure 7:
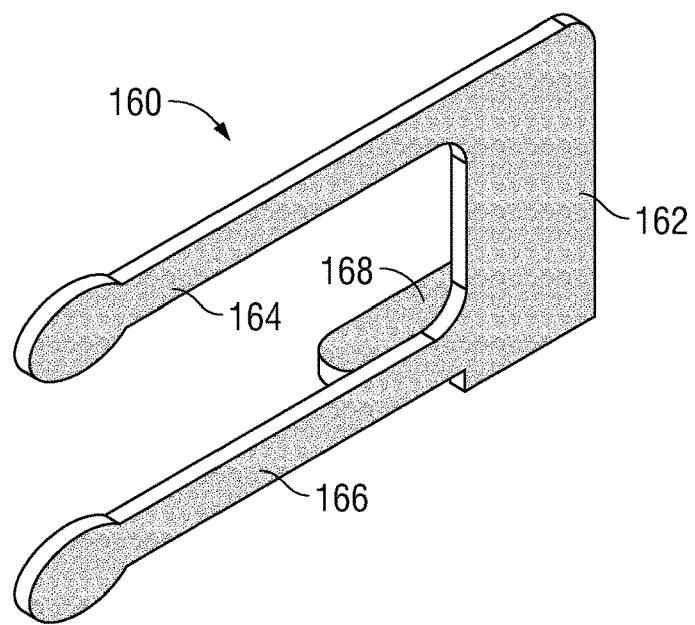
FIG. 7 is an isometric view of an attachment member of the ET tube securement device.

Referring to FIGS. 7-9, attachment member 160 of first portion 100 of ET securement device 10 is formed from or includes a section of hook and/or loop material or other suitable releasable self-adhering or self-engaging material (including material with discrete structures such as snaps, buttons, etc.). Attachment member 160 includes a body 162, first and second spaced-apart arms 164, 166 extending from a side of body 162 within a plane defined by body 162, and a base 168 extending from a bottom end of body 162 within a plane perpendicular to the plane defined by body 162. In embodiments, arms 164, 166 may extend from opposite sides of body 162 rather than the same side thereof as illustrated.

Body 162 is configured to be attached, e.g., adhered, attached by hook and loop engagement, etc., to rear face 114b of body 112 of vertical support 110 while arms 164, 166 are wrapped around vertical support 110 and the ET tube "ET" engaged within vertical support 110 to engage themselves and/or one another to retain the ET tube "ET" within vertical support 110. Base 168 of attachment member 160 is configured to be attached, e.g., adhered, to foot 120 of vertical support 110 and extends perpendicularly relative to body 112 of vertical support 110 similarly as foot 120. Base 168 of attachment member 160 includes hook and/or loop structure on the exposed, bottom-facing surface thereof, e.g., the face opposite the face that is engaged with foot 120. Arms 164, 166 likewise include hook and/or loop structure on portions or the entireties thereof.

Turning to FIGS. 10 and 11, the second portion 200 of the ET securement device 10 includes a piece of material 210 including hook and/or loop structure on a first face thereof and an adhesive layer, e.g., including a silicone adhesive, disposed on the second, opposing face thereof. The piece of material 210 may define a C-shaped configuration or any other configuration wherein the piece of material 210 may be positioned to substantially surround a patient's mouth without obstruct the patient's mouth. The side opening defined by the C-shaped piece of material 210 is advantageous in that it enables application around a patient's mouth and about the ET tube "ET," since it is typically applied after the ET tube "ET" is installed into the patient's trachea.

The adhesive layer on the second face of the piece of material 210 enables the piece of material 210 to be adhered to the patient's face. The hook and/or loop structure on the first face of the piece of material 210 enables releasable engagement with the hook and/or loop structure of base 168 of attachment member 160, thereby enabling releasable engagement of the first portion 100 of the ET securement device 10 with the second portion 200 of the ET securement device 10, thus retaining the ET tube "ET" engaged by the first portion 100 in position relative to the patient.

A method of installing ET securement device 10 (FIGS. 10 and 11) on a patient's face and in engagement with ET tube "ET" to support the ET tube "ET" relative to a patient is detailed below with general reference to FIGS. 4-11. Although necessarily described in an order, it is contemplated that the various steps be performed in any suitable order, depending upon a particular purpose, preference, and/or other reason. Further, although illustrated with respect to an infant, the devices and methods of the present disclosure may likewise be used with other human and/or animal patients.

The ET tube "ET" is typically first installed into the patient's trachea. Next, in order to secure the ET tube "ET" in position, first portion 100 of ET securement device 10 is engaged about the ET tube "ET," second portion 200 of ET securement device 10 is attached to the patient, and first and second portions 100, 200 are attached to one another.

With respect to engagement of first portion 100 of ET securement device 10 about the ET tube "ET," the ET tube "ET" is engaged within vertical support 110 via manipulating the ET tube "ET" in multiple directions such that the ET tube "ET" is engaged within and extends from guide 124 at top end 114e of body 112 of vertical support 110, through tortuous channel 130 defined by posts 116 of vertical support 110, to guide 128 at bottom end 114f of body 112 of vertical support 110. The ET tube "ET" is also curved, due to V-shaped protrusion 134 of vertical support 110, whereby the gap "G" is maintained between the central portion of the ET tube "ET" and front face 114a of body 112 of vertical support 110, while ET tube "ET" is received within the saddles defined by U-shaped guides 124, 128 at the top and bottom ends 114e, 114f, respectively, of body 112 of vertical support 110.

Once ET tube "ET" is engaged within vertical support 110, attachment member 160 is attached to vertical support 110 and arms 164, 166 of attachment member 160 are wrapped around vertical support 110 and the ET tube "ET" engaged within vertical support 110 to engage themselves and/or one another to retain the ET tube "ET" within vertical support 110. More specifically, the upper arm 164 may be wrapped circumferentially about a portion of ET tube "ET" towards top end 114e of body 112 of vertical support 110 while the lower arm 166 is wrapped circumferentially about a portion of ET tube "ET" towards bottom end 114f of body 112 of vertical support 110, parallel and spaced-apart from upper arm 164. However, other configurations are also contemplated.

With respect to attachment of second portion 200 of ET securement device 10 is attached to the patient, the piece of material 210 of second portion 200 is adhered to the patient's face to substantially surround the patient's mouth without obstruct the patient's mouth. Thereafter, the base 168 of the attachment member 160 of the first portion 100 may be engaged with the piece of material 210 of the second portion 200, e.g., via hook and loop fastener engagement, thereby releasably engaging the first portion 100 of the ET securement device 10 with the second portion 200 of the ET securement device 10, thus retaining the ET tube "ET" engaged in position relative to the patient.

Figure 12:
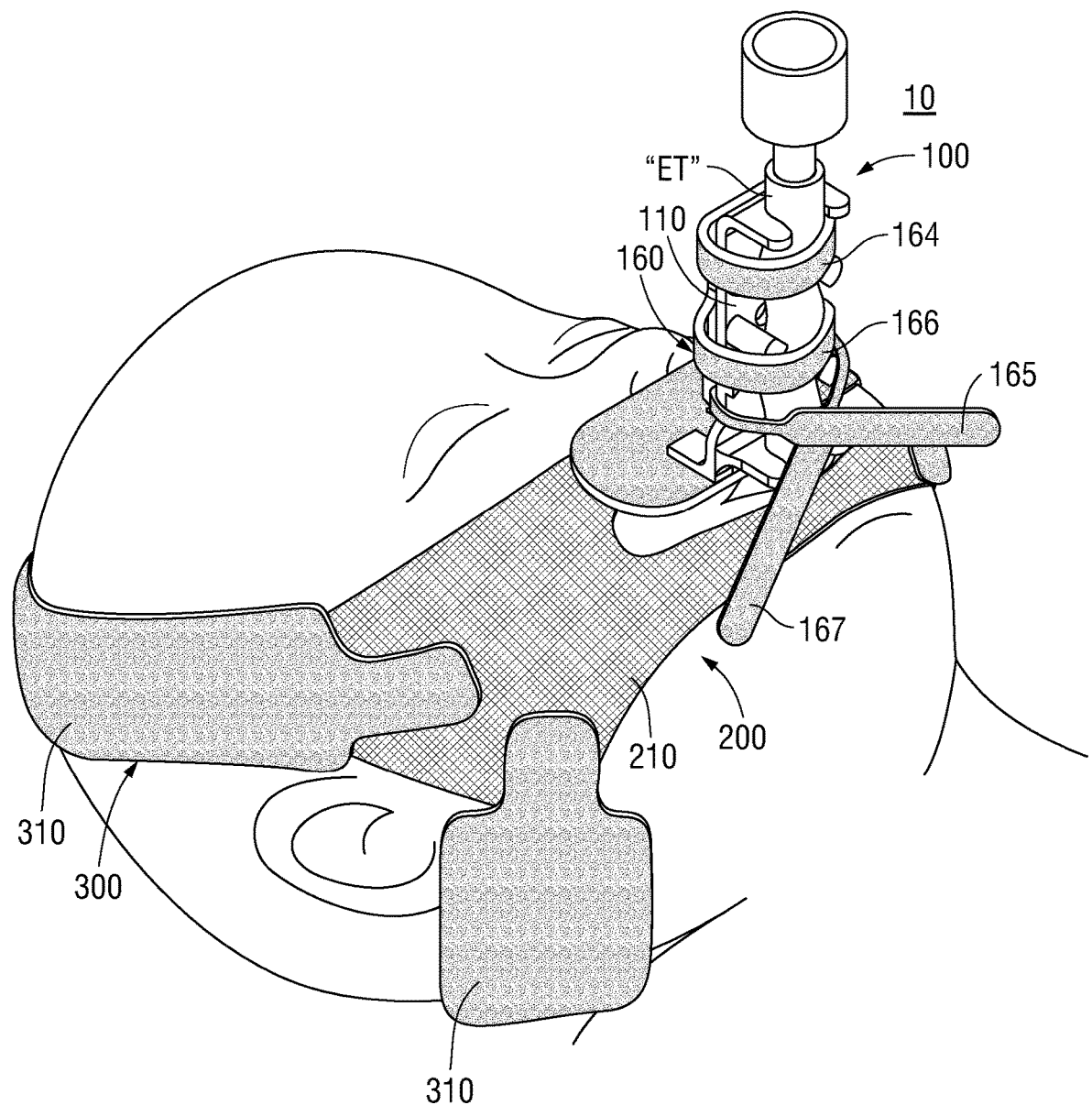
FIG. 12 is a perspective view illustrating another ET tube securement device provided in accordance with the present disclosure secured in position on an infant's face retaining an ET tube extending into the infant's mouth.
Figure 13:
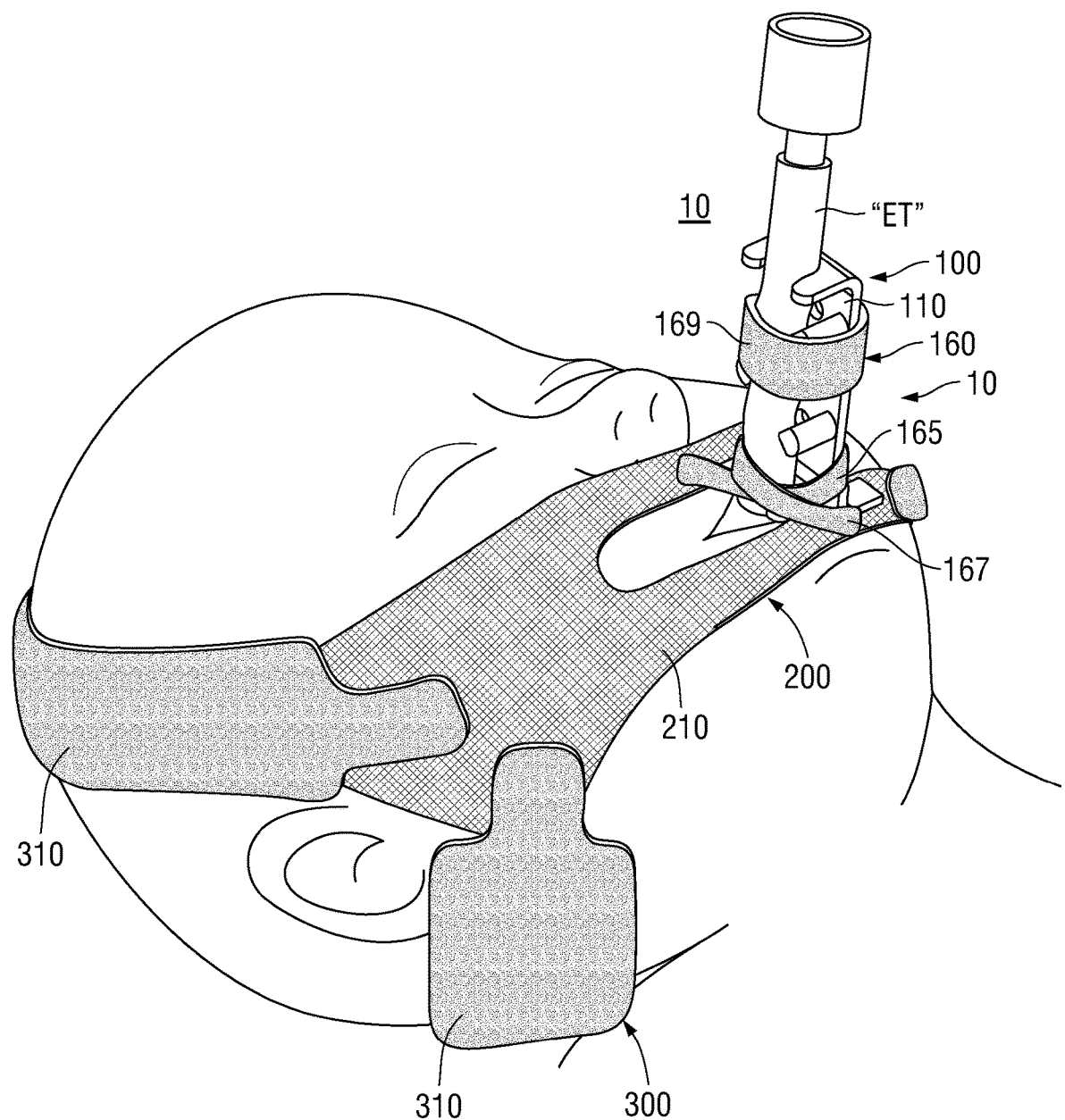
FIG. 13 is a perspective view illustrating the ET tube securement device of FIG. 12 secured in position on an infant's face in an alternate orientation, retaining an ET tube extending into the infant's mouth.

Turning to FIG. 12, in embodiments, attachment member 160 may define a different configuration wherein, rather than being wrapped around vertical support 110 and the ET tube "ET" such that the arms thereof engage themselves and/or one another, the arms 164, 166 and/or an additional arms 165, 167 may be configured to wrap around vertical support 110 and the ET tube "ET" and engage e.g., via hook and loop fastener engagement, the piece of material 210. In such embodiments, some of the arms, e.g., arms 164, 166, may engage themselves and/or one another, while other arms, e.g., additional arms 165, 167, wrap about vertical support 110 and the ET tube "ET," cross one another, and engage the piece of material 210. The arms 164, 166 and/or additional arms 165, 167 may extend from the same and/or different sides of attachment member 160, e.g., wherein arm 164 and additional arm 165 extend from one side while arm 166 and additional arm 167 extend from an opposite side. Additionally or alternatively, one or more of arms 164, 166 and/or additional arms 165, 167 may be separate components, e.g., wherein arms 164, 166 extend from opposing sides of attachment member 160 while additional arms 165, 167 are connected to one another but separate from attachment member 160 (see FIG. 12). In still other embodiments, arms 164, 166 may be joined to define a single arm 169 (see FIG. 13).

Continuing with reference to FIG. 12, in additional or alternative embodiments, the piece of material 210 may define an expanded configuration and/or be supported by a support 300 including one or more head straps 310 instead of (or in addition to) being adhered to the patient's face. With respect to the expanded configuration, the piece of material 210 may define a suitable width to extend laterally beyond the patient's eyes and around the patient's head towards the ears, on both sides. Non-expanded configurations (see FIGS. 10-11) or other suitable configurations are also contemplated.

Head straps 310 are configured to releasably engage e.g., via hook and loop fastener engagement, the piece of material 210 at opposing sides thereof and extend atop and/or around the patient's head. In embodiments, a first strap 310 is positioned above the patient's ears and extends over the top of the patient's head to engage the piece of material 210 at opposing sides thereof while a second strap 310 is positioned below the patient's ears and extends around the back of the patient's head to engage the piece of material 210 at opposing sides thereof. In other embodiments, the straps 310 are crisscrossed at the back of the patient's head, e.g., wherein each strap is engaged to the piece of material 210 below the patient's ear on one side and above the patient's ear on the other side. In still other embodiments, the support 300 further includes a bonnet body (not shown) configured to surround at least a portion of the back of the patient's head, with two pairs of head straps 310 extending therefrom, one pair from each side of the bonnet body (not shown), e.g., one strap 310 on each side extending around the patient's head below the ear and the other strap 310 on each side extending around the patient's head above the ear.

As illustrated in FIGS. 11 and 12, the first portion 100 of ET securement device 10 is engaged with the second portion 200 of ET securement device 10 positioned such that the first portion 100 is generally centered relative to the second portion 200 and the patient's mouth and oriented with the ET tube "ET" further towards the chin of the patient as compared to body 112 of vertical support 110, which is disposed further towards the forehead of the patient. As an alternative, with reference to FIG. 13, the first portion 100 of ET securement device 10 may be engaged with the second portion 200 of ET securement device 10 such that the ET tube "ET" is positioned further towards one ear of the patient as compared to body 112 of vertical support 110, which is disposed further towards the other ear of the patient. In embodiments, first portion 100 of ET securement device 10 may be may be engaged with the second portion 200 of ET securement device 10 in any suitable orientation and/or position (e.g., offset towards one side of the patient's mouth and/or offset relative to a center of the second portion 200). In some instances, it may be beneficial to move first portion 100 to different orientations and/or positions relative to second portion 200, e.g., to prevent palate grooving.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A securement device for securing an endotracheal (ET) tube relative to a patient, the securement device comprising:
    a vertical support, including:
        a body defining first and second faces, first and second sides, and top and bottom ends;
        a plurality of posts extending from the first face of the body to define a tortuous path extending from the top end of the body to the bottom end of the body;
        first and second guides disposed at or adjacent the top and bottom ends, respectively, of the body and defining an entry and an exit, respectively; and
        a protrusion protruding from the first face of the body and defining at least first and second segments, wherein the first and second segments of the protrusion extend across the tortuous path,
        wherein the vertical support is configured to engage the ET tube at the entry via the first guide, within the tortuous path via the plurality of posts, and at the exit via the second guide, and wherein the protrusion is configured to maintain a minimum gap between a portion of the ET tube and the front face of the body;
    an attachment member attached to the vertical support and including at least one arm, the at least one arm configured to wrap around the vertical support to retain the ET tube therein, and
    a piece of material configured for positioning on the face of the patient at least partially surrounding the mouth of the patient, wherein the vertical support further includes a foot extending from the second face of the body in perpendicular orientation relative to the body, wherein the attachment member further includes a base attached to the foot, and wherein the base of the attachment member is configured to releasably engage the piece of material to thereby releasably engage the vertical support to the piece of material.

2. The securement device according to claim 1, wherein the attachment member is configured to releasably engage the piece of material via hook and loop engagement.

3. The securement device according to claim 1, wherein the piece of material includes an adhesive layer configured to adhere to the face of the patient.

4. The securement device according to claim 1, further comprising a support including at least one strap configured to wrap at least partially around the head of the patient and engage the piece of material to retain the piece of material on the face of the patient.

5. The securement device according to claim 1, wherein the first and second segments of the protrusion define a V-shaped protrusion.

6. A securement device for securing an endotracheal (ET) tube relative to a patient, the securement device comprising:
    a first portion, including:
        a vertical support including a body, a foot extending from the body, a plurality of posts extending from the body to define a tortuous path extending from a top of the body to a bottom of the body, and first and second guides disposed at or adjacent the top and the bottom, respectively, of the body and defining an entry and an exit, respectively, wherein the vertical support is configured to engage the ET tube at the entry via the first guide, within the tortuous path via the plurality of posts, and at the exit via the second guide; and
        an attachment member including a base attached to the foot of the vertical support, and at least one arm, the at least one arm configured to wrap around the vertical support to retain the ET tube therein; and
    a second portion, including:
        a piece of material configured for positioned on the face of a patient at least partially surrounding the mouth of the patient, the base of the attachment member configured to releasably engage the piece of material; and a support including at least one strap configured to wrap at least partially around the head of the patient and engage the piece of material to retain the piece of material on the face of the patient, wherein the first portion is configured to releasably engage the second portion.

7. The securement device according to claim 6, wherein the attachment member is configured to releasably engage the piece of material via hook and loop engagement.

8. The securement device according to claim 6, wherein one of the at least one arm is configured to wrap around the vertical support and engage the piece of material.

9. The securement device according to claim 6, wherein the vertical support further includes a protrusion extending from the body, the protrusion configured to maintain a minimum gap between a portion of the ET tube and the body.

10. The securement device according to claim 9, wherein the protrusion includes at least first and second segments that extend across the tortuous path.

11. A method of securing an endotracheal (ET) tube extending into the mouth of a patient relative to the patient, comprising:

positioning a piece of material about the mouth of the patient and the ET tube extending into the mouth of the patient;

engaging a vertical support to the ET tube such that the ET tube extends through a tortuous path defined by the vertical support and is maintained a minimum gap distance from a front face of the vertical support via a continuous protrusion protruding from the front face of the vertical support and crossing the tortuous path at least two times;

wrapping at least one first arm about at least a portion of the vertical support and the ET tube to secure the ET tube; and releasably engaging the vertical support with the piece of material to thereby retain the ET tube relative to the patient.

12. The method according to claim 11, wherein engaging the vertical support with the piece of material includes at least one of:

releasably engaging a base of an attachment member that is attached to the vertical support of the piece of material; or wrapping at least one second arm about at least a portion of the vertical support and the ET tube and releasably engaging the at least one second arm to the piece of material.

13. The method according to claim 12, wherein at least one of the releasable engagement of the base to the piece of material, or the releasable engagement of at least one strap to the piece of material includes a hook and loop engagement.

14. The method according to claim 11, further comprising:

positioning a support including at least one strap at least partially around the head of the patient; and releasably engaging the at least one strap with the piece of material to retain the piece of material on the face of the patient.

15. The method according to claim 11, further comprising:

disengaging the vertical support from the piece of material and subsequently reengaging the vertical support with the piece of material in at least one of a different position or a different orientation.

16. The method according to claim 11, wherein engaging the vertical support to the ET tube further includes engaging the ET tube within first and second guides at top and bottom ends, respectively, of the vertical support.

* * * * *